(12) United States Patent
Clemen, Jr.

(10) Patent No.: US 9,002,022 B1
(45) Date of Patent: Apr. 7, 2015

(54) METHODS FOR NON-DESTRUCTIVE INSPECTION OF THICK FIBER-REINFORCED COMPOSITE PARTS

(75) Inventor: Mark J. Clemen, Jr., Bremerton, WA (US)

(73) Assignee: The Boeing Company, Chicago, IL (US)

( * ) Notice: Subject to any disclaimer, the term of this patent is extended or adjusted under 35 U.S.C. 154(b) by 752 days.

(21) Appl. No.: 13/269,044

(22) Filed: Oct. 7, 2011

(51) Int. Cl.
*H04R 29/00* (2006.01)

(52) U.S. Cl.
CPC .................... *H04R 29/00* (2013.01)

(58) Field of Classification Search
CPC .................... H04R 29/00; H01L 41/00
USPC .................... 381/396, 123, 421, 59
See application file for complete search history.

(56) References Cited

U.S. PATENT DOCUMENTS

| | | | |
|---|---|---|---|
| 4,755,707 A * | 7/1988 | Nakaya et al. | 310/334 |
| 6,806,622 B1 * | 10/2004 | Schmidt et al. | 310/334 |
| 7,010,143 B2 * | 3/2006 | Kam | 381/426 |
| 7,513,147 B2 | 4/2009 | Yogeswaren | |
| 7,690,259 B2 | 4/2010 | Bui et al. | |
| 8,155,326 B2 * | 4/2012 | Schweitzer et al. | 381/56 |
| 2005/0031130 A1 * | 2/2005 | Devantier et al. | 381/58 |
| 2011/0188699 A1 * | 8/2011 | Shibaoka et al. | 381/428 |

OTHER PUBLICATIONS

Piezo Film Sensors, Technical Manual, Measurement Specialties, Inc., Apr. 1999.
Li et al., "Fabrication and Characterization of Amorphous Magnetostrictive Nanobars and Nanotubes," Materials Research and Education Center, Auburn University, Auburn, AL.

* cited by examiner

*Primary Examiner* — Disler Paul
(74) *Attorney, Agent, or Firm* — Ostrager Chong Flaherty & Broitman P.C.

(57) ABSTRACT

A fiber-reinforced composite part comprises structural fiber strands and linear electromagnetic-to-acoustic transducers embedded in a polymeric matrix. When these internal transducers are activated in sequence, the propagating acoustic waves are detected by an array of external acoustic-to-electric transducers acoustically coupled to external surfaces of the part. These external transducers convert impinging acoustic waves into electrical signals that carry information concerning acoustic wave amplitudes and phase shifts relative to the excitation of the internal transducers. The electrical signals are processed by a computer which is programmed to determine the location and orientation of each internal transducer and ultimately the structural integrity of the composition.

23 Claims, 3 Drawing Sheets

METHODS FOR NON-DESTRUCTIVE INSPECTION OF THICK FIBER-REINFORCED COMPOSITE PARTS

BACKGROUND

The present invention relates generally to systems and methods for inspecting a structure. More particularly, the embodiments disclosed herein relate to systems and methods for non-destructive inspection of parts made of fiber-reinforced composite material.

Fiber-reinforced composite materials comprise fibers embedded in a matrix material, such as thermoset and thermoplastic polymer resins. As is well known, a composite laminate is constructed with multiple (e.g., 20) plies. For a conventional ply of a flat laminate, each ply has fiber paths which are described entirely by ply angles selected from the group consisting of 0°, ±45° and 90°. However, pairs of 0° plies or ±45° plies in a conventional laminate may be replaced with pairs of steered-fiber plies, the plies of each pair being balanced. The steered-fiber plies of each pair may be separated by one or more intervening conventional plies.

It is increasingly common practice to manufacture aerospace parts from lightweight, high-strength fiber-reinforced composite materials, such as carbon-fiber epoxy composites. Each carbon fiber strand is a bundle of many thousand carbon filaments. A single such filament is a thin tube with a diameter of 5-8 micrometers and consists almost exclusively of carbon. Thick, complex carbon-fiber epoxy composites are difficult to uniformly produce, and susceptible to internal movements and shifts during curing. These problems mitigate the strength and reliability of fiber-reinforced composite parts, and become more pronounced during curing of thick parts such as helicopter blades or aircraft structural joints.

Evaluation of such finished composite parts is difficult. The qualification of complex parts after manufacturing requires non-destructive evaluation (NDE) that is able to identify the occurrence and frequency of such defects as air bubbles/voids, ripples or waves in the fiber alignment, and balling or bunching of fibers, especially near the ends of layout fiber runs.

Common NDE methods have difficulty in imaging subtle fiber orientations in thick epoxy parts. Present methods inject energy—acoustic, electromagnetic, x-ray radiation or magnetic field—and then infer the internal structure of complex parts by the resulting energy coming back out. Ultrasound works well for finding bubbles and arguably epoxy pooling, but is insensitive to carbon fiber waviness. X-rays are insensitive to distinguishing carbon fibers and epoxy. Carbon fibers absorb and dissipate electromagnetic energy, precluding high-resolution studies of thick parts. Magnetic resonance imaging is expensive, onerous and requires that the entire part be placed into the imaging machine.

There is a need for systems and methods for accurate non-destructive inspection of fiber-reinforced composite parts for incorporation into larger structures during assembly.

SUMMARY

This disclosure is directed to the non-destructive inspection of fiber-reinforced composite parts using ultrasonic waves that are generated within the composite material itself. In accordance with the broad concept disclosed herein, electromagnetic-to-acoustic transducers are embedded in a polymeric matrix of the composite part, while acoustic-to-electric transducers are placed adjacent to the external surfaces of the part. The electromagnetic-to-acoustic transducers (also referred to herein as "internal transducers") are pulsed in sequence to produce acoustic waves that propagate through the composite part. The acoustic-to-electric transducers (also referred to herein as "external transducers") detect impinging acoustic waves and transduce them into electrical signals that are sent to a computer for processing. The characteristics (e.g., amplitude and phase shift) of the propagating acoustic waves can be exploited to externally trace fiber orientation and position with the fiber-reinforced composite part. Ultrasonic scattering off of internal voids or bubbles can also be detected.

In accordance with some embodiments disclosed hereinafter, the electromagnetic-to-acoustic transducers comprise pairs of transducing fiber strands separated by piezoelectric or magnetostrictive material and embedded in a polymeric matrix which also has structural fiber strands embedded therein (many more structural fiber strands than transducing fiber strands). Within each layer (or only some layers) of the composite laminate, a multiplicity of such transducing fiber strands are interleaved with and parallel to the structural fiber strands in that layer.

After the lay-up has been cured, the cured part can be examined non-destructively by exciting individual transducing fiber strands embedded in the composite part (e.g., by the application of a pulsed electromagnetic field) to emit acoustic waves that propagate throughout the composite part in all directions. Those propagating acoustic waves are detected by an array of external acoustic-to-electric transducers. Microphones, ultrasonic sensors or other types of acoustic-electric transducers can be utilized. These external transducers convert impinging acoustic waves into electrical signals that carry information concerning acoustic wave amplitudes and phase shifts relative to the excitation of the internal acoustic transducers.

The electrical signals from the external transducers are processed by a computer which is programmed to determine the location and orientation of each transmitting internal transducer and ultimately the structural integrity of the composition. In particular, imaging tomography is applied to the data to produce a three-dimensional map of the internal transducer layouts. Unusual phase shifts and acoustic scattering also can be exploited to map internal bubble locations and sizes.

The methodology disclosed herein separates the problem of signal generation from that of signal detection: the signals are generated by acoustic source fibers that are a part of the composite layup. These internal transducers are excited in sequence and their position and orientation are externally traced to gauge the quality and consistency of the final cured part. In one particular application, this methodology can be used to qualify composite parts for incorporation into larger structures (e.g., aircraft) during assembly, thereby combining the manufacturing of fiber-reinforced composite parts with the qualification testing of those parts once cured.

As will be described in more detail below, one aspect of the invention is a fiber-reinforced composite part comprising a multiplicity of plies, wherein at least one of the multiplicity of plies comprises: a polymeric matrix; a multiplicity of structural fiber strands embedded in the polymeric matrix; and a multiplicity of linear electromagnetic-to-acoustic transducers embedded in the polymeric matrix and interleaved with the structural fiber strands.

Another aspect of the invention is a method for non-destructive inspection of a composite part, comprising: (a) activating a multiplicity of linear acoustic sources embedded in a polymeric matrix of the composite part in sequence, thereby causing acoustic waves to emanate from each acoustic source and propagate toward external surfaces of the composite part; and (b) transducing acoustic waves received at external surfaces of the composite part into electric signals having characteristics indicative of the run of each acoustic source.

A further aspect of the invention is a system comprising: a composite part comprising a multiplicity of plies, wherein each of the multiplicity of plies comprises a polymeric matrix and a multiplicity of linear electromagnetic-to-acoustic transducers embedded in the polymeric matrix; a pulser for outputting pulsed electrical energy; a multiplicity of switches connected to the pulser and respectively connected to the linear electromagnetic-to-acoustic transducers, each of the switches electrically coupling a respective linear electromagnetic-to-acoustic transducer to the pulser when the switch is closed and the pulser is outputting pulsed electrical energy; and a computer system programmed to control the switches to select which linear electromagnetic-to-acoustic transducer receives pulsed electrical energy from the pulser.

Other aspects of the invention are disclosed and claimed below.

BRIEF DESCRIPTION OF THE DRAWINGS

Various embodiments will be hereinafter described with reference to drawings for the purpose of illustrating the foregoing and other aspects of the invention.

Reference will hereinafter be made to the drawings in which similar elements in different drawings bear the same reference numerals.

DETAILED DESCRIPTION

Figure 1:
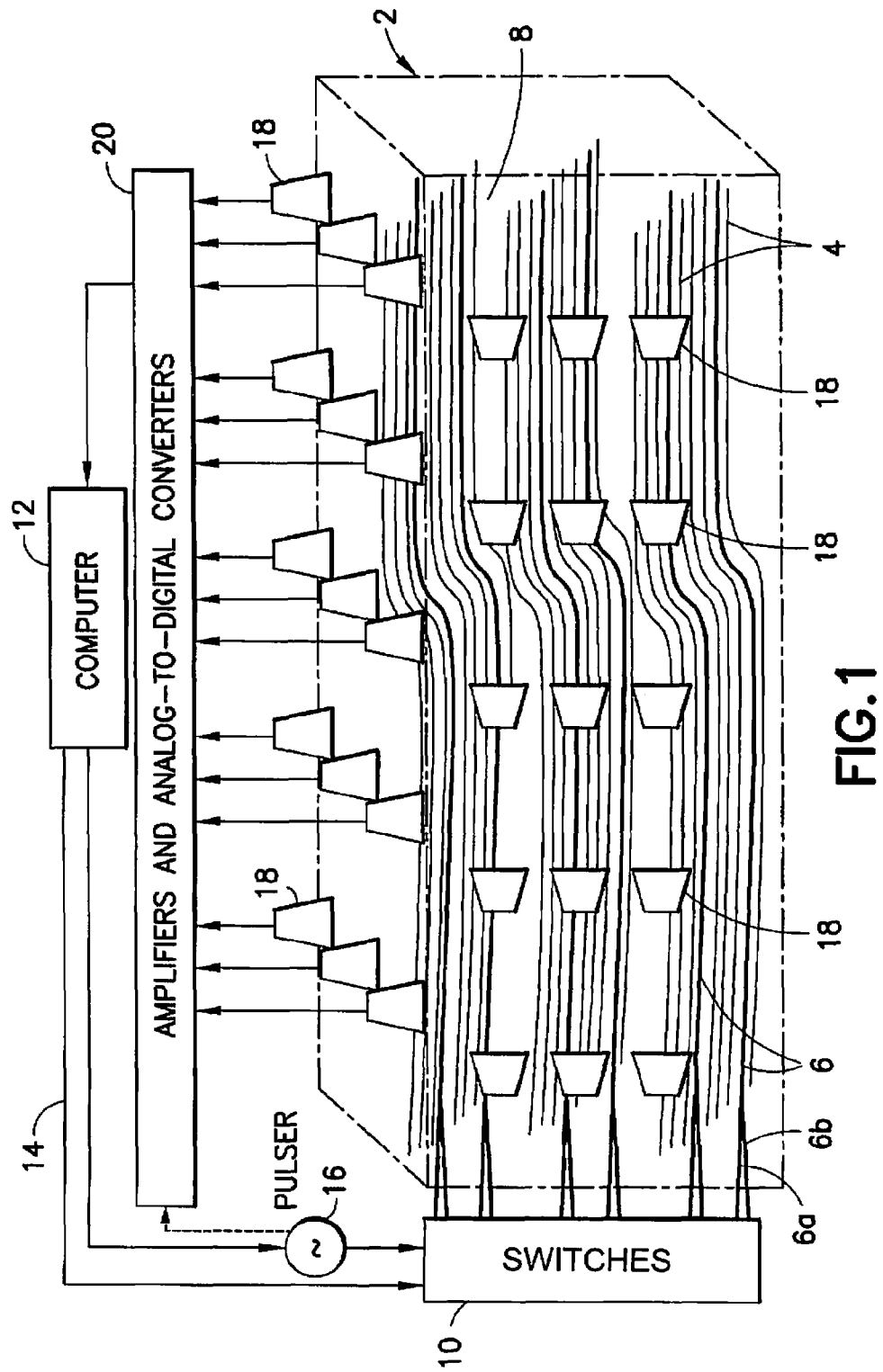
FIG. 1 is a diagram showing a system for non-destructive evaluation of a composite part in accordance with one embodiment.

A system for non-destructive evaluation of fiber-reinforced composite parts in accordance with one embodiment will now be described with reference to FIG. 1, which shows a fiber-reinforced composite part 2 comprising structural fiber strands 4 and electromagnetic-to-acoustic transducers 6 (hereinafter "internal transducers") embedded in a polymeric matrix 8. The internal transducers 6 are built in one or more plies of the lay-up of the fiber-reinforced composite part 2. In accordance with some embodiments disclosed below, the internal transducers 6 are pairs of transducing structural fiber strands (e.g., yarn comprising carbon filaments) coated or otherwise separated by piezoelectric or magnetostrictive material and embedded in the polymeric matrix 8 of the cured composite part 2. There are many more structural fiber strands 4 than transducing fiber strands 6.

As will be explained in more detail later with reference to FIGS. 2-5, the internal transducers 6 may take the form of pairs of electrically conductive fiber strands (optionally supplemented with nanotubes) coated or otherwise separated by piezoelectric or magnetostrictive insulating material. Alternatively, the internal transducers 6 may take the form of pairs of electrically conductive fiber strands supplemented with nanotubes made of magnetostrictive material, the fiber strands being coated or otherwise separated by electrically insulating material. The internal transducers 6 may take any form that generates an acoustic wave in response to a voltage or current pulse but which will not degrade the structural strength of the composite material.

Referring to FIG. 1, each internal transducer 6 comprises first and second electrical conductors 6a, 6b. One end of each electrical conductor 6a, 6b is connected to a multiplicity of switches 10, which is controlled by a computer 12 via electrical control signals sent via a multiplicity of conductors generally indicated by line 14 in FIG. 1. Each internal transducer 6 is selected in turn by computer 12 via switches 10. The switches 10 may be configured to function as a multiplexer. When selected, each internal transducer 6 is connected to a pulser 16, thereby causing the selected internal transducer 6 to produce an electromagnetic field within the polymeric matrix 8. This electromagnetic field in turn causes the piezoelectric or magnetostrictive material incorporated in the selected transducer 6 to produce an acoustic wave. Each pulse results in a respective acoustic wave emanating along a line corresponding to the run of the selected transducer 6 and propagating through the polymeric matrix 8. In response to control signals from computer 12, the switches 10 connect the pulser 16 to the internal transducers 6 in sequence. The operation of pulser 16 is likewise controlled by computer 12.

The system shown in FIG. 1 further comprises an array of acoustic-to-electric transducers 18 which are disposed adjacent to and acoustically coupled (in well-known manner) with the external surfaces of the fiber-reinforced composite part 2. Although FIG. 1 shows only acoustic-to-electric transducers arranged on the top and front external surfaces of composite part 2, identical acoustic-to-electric transducers are also arranged adjacent to the bottom and rear external surfaces of the composite part 2.

The acoustic-to-electric transducers 18 (hereinafter "external transducers") detect the line of sound emanating from the selected internal transducer 6 when that sound signal reaches the part surface. Each external transducer 18 may, for example, comprise a microphone or an ultrasonic detector. The external transducers 18 detect the impinging sound signal and transduce that sound signal into an electrical signal. Each external transducer 18 may be connected to a respective one of a multiplicity of amplifiers. The amplifiers increase the amplitude of the electrical detection signals. Those electrical signals are then converted from analog to digital by means of respective analog-to-digital converters, again one per external transducer 18. The resulting digital signals are received by computer 12 for processing. To avoid clutter, FIG. 1 only shows amplifiers and analog-to-digital converters 20 electrically connected to the external transducers 18 on the top surface of composite part 2. However, the external transducers on the front, rear and bottom external surfaces of composite part 2 are also electrically connected to respective amplifiers and analog-to-digital converters, which return digital amplified electrical signals to computer 12. These signals have characteristics indicating the amplitudes of the sound waves detected by the external transducers 18 and their phase shifts relative to the phase of the excitation pulses output by the pulser 16.

The total magnitude of the received signal at each external transducer 18 through a lossy medium (i.e., a medium in which acoustic energy is absorbed without propagating very deeply) such as a composite laminate enables tracking the run of the emitting internal transducer 6 through the composite part 2. Because the composite part 2 is fabricated using plies in which the structural fiber strands 4 and the linear internal transducers 6 are mutually parallel, the position of the emitting internal transducer 6, including changes in orientation that occur along its length during fabrication, is indicative of the position and orientation of adjacent structural fiber strands 4. The position of the emitting internal transducer 6 in between two receiving external transducers 18 may be interpolated from the total magnitude of the received signal in any one dimension; for example, in the x direction this would be:

$$\eta_i = \frac{A_i x_i + A_{i+1} x_{i+1}}{A_i + A_{i+1}}$$

where $A_i$ is the total amplitude of the received signal at the i-th sensor, $A_{i+1}$ is the total amplitude of the received signal at its neighbor, $x_i$ is the x coordinate of the i-th sensor, and $x_{i+1}$ is the x coordinate of the neighboring (i.e., (i+1)-th) sensor. The two relevant sensors in any one dimension are those that are known to roughly follow the direction of the part and receive acoustic signals that have the greatest amplitude.

Where the time history of the received signal at each sensor is available, then it is also possible to divide the received signal into the direct run response and the indirect path response. The direct run signal magnitude can be exploited (as described above) to interpolate the position of the emitting internal transducer, and the indirect run response (the received signal arising from the pulsed excitation of the transmitting internal transducer that arrives after the initial received response) can be attributed to acoustic scattering on features within the laminate. This late signal may be exploited to judge the size and position of such scattering features.

In accordance with a known method employed in real-time signal processing, the signals output by each sensor or microphone 18 can be amplified using phase lock amplifiers. These phase lock amplifiers receive signals from pulser 16 indicating the times of the respective pulses by way of an electrical conductor (indicated by the dashed arrow in FIG. 1) that extends from pulser 16 to block 20. The phase lock amplifiers may increase the signal-to-noise ratio in a thick composite part. Furthermore, the phase (effectively the time at some frequency) of the received acoustic signal may be varied at each external transducer 18 with respect to the initial pulse time and then features within the part 2 can be interpolated at each selected phase to build up a map of the internal structure. Thus the interleaved acoustic sources (i.e., internal transducers 6) inside the composite part 2 enable a map of the internal structural fiber layout, including wiggles or waviness and bunching near the ends of the fibers. The map or other results can displayed on a monitor (not shown in FIG. 1) which is connected to the computer.

When time or phase information is available from each sensor with respect to the transmitting internal transducer, then other standard tomography algorithms may be applied on the received signals. Exemplary tomography algorithms are disclosed, for example, in the following references: (1) Herman, Gabor T., "Fundamentals of Computerized Tomography: Image Reconstruction from Projections", $2^{nd}$ Edition, Springer Dordrecht, London, 2009; and (2) Natterer, F., "Mathematics of Computerized Tomography", Society for Industrial and Applied Mathematics, July 2001.

At ultrasonic frequencies, some microphones or sensors will also detect sound reflected and scattered from internal bubbles or voids which will act to "smear out" the apparent interpolated location of the line source. This may be flagged as a problem area by computer 12.

As noted above, phase-locked amplification of sensed ultrasonic frequencies may improve the signal-to-noise ratio of the detected signal. The computer 12 may also be programmed to vary the phasing of the phase-locking, especially at ultrasonic frequencies, to further enhance those signals that appear out of phase in some microphones or sensors with respect to the driven signal. This effect may occur due to scattering from voids or from kinks or waves in the excited internal transducer as it runs through the part, and can be exploited to show smaller flaws than may otherwise be resolved.

Figure 2:
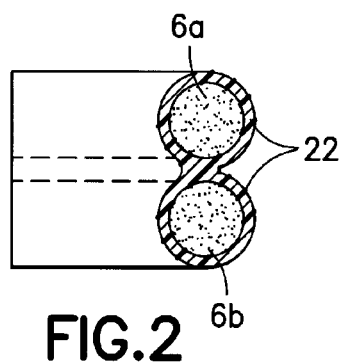
FIG. 2 is a diagram showing a side view with cross section of a pair of coated electrically conductive fiber strands fused together along their length by a coating made of piezoelectric material.

The acoustic sources embedded in the composite material may be constructed in different ways. One exemplary construction is shown in FIG. 2. In accordance with this embodiment, each acoustic source comprises a pair of fiber strands 6a, 6b (made of electrically conductive material) coated with a piezoelectric material 22 (such as polarized PVDF), the coatings 22 being fused together in the space separating the paired fiber strands. In response to pulsation, the electric field produced by the fiber strand pairs 6a, 6b due to the electric voltage pulse from the pulser is converted to mechanical vibration of the piezoelectric material 22, which mechanical vibration in turn produces acoustic waves that propagate through the composite material.

Figure 3:
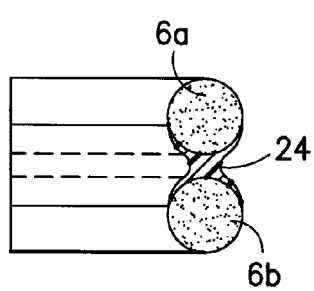
FIG. 3 is a diagram showing a side view with cross section of a pair of partially coated electrically conductive fiber strands fused together along their length by a partial coating made of piezoelectric material.

Another exemplary construction is shown in FIG. 3. In accordance with this embodiment, each acoustic source comprises a pair of uncoated fiber strands 6a, 6b (made of electrically conductive material) which are held together, separated and electrically insulated from each other by piezoelectric material 24. In this embodiment, a major portion of the surface area of each fiber strand 6a, 6b is bare to the surrounding epoxy medium to maximize structural strength. In response to a voltage pulse from the pulser, an electric field is produced between the fiber strands 6a and 6b, which in turn induces the piezoelectric material 24 to generate an acoustic wave that propagates through the surrounding matrix of the composite part.

Alternatively, a pair of small-gauge electrically conductive fiber strands coated with piezoelectric material can be twisted together to form an acoustic source. In accordance with a further alternative, an electric-to-acoustic transducer may be implemented as a coaxial microcable with two electrical conductors, the dielectric filler of the coaxial microcable being the piezoelectric material.

Conventional wisdom in the manufacture of fiber-composite aerospace parts holds that the incorporation of any fiber or component not directly supporting the structural integrity of the composite part is an added risk to failure and must be avoided. In accordance with the above-described embodiments, the fiber strands of each acoustic source may be the same as the structural fibers strands 4. For example, the fiber strands 6a, 6b shown in FIGS. 2 and 3 may incorporate the same carbon fiber strands normally used in aerospace manufacturing, though with the added acoustic source such as polarized PVDF insulation separating the paired fiber strands. In addition, the strength of carbon fiber strands can be enhanced by the addition of carbon nanotubes.

Figure 4:
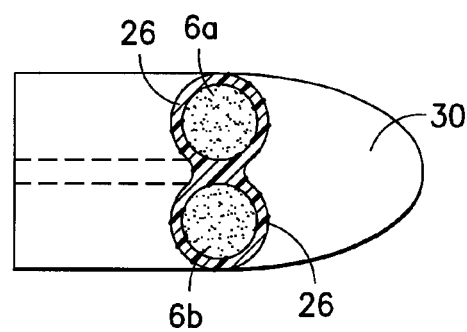
FIG. 4 is a diagram showing a side view with cross section of a pair of coated electrically conductive fiber strands fused together along their length by a coating made of magnetostrictive material. These electrically conductive fiber strands are shorted at their ends.

Another exemplary construction of the acoustic sources is shown in FIG. 4. In accordance with this embodiment, each acoustic source comprises a pair of fiber strands 6a, 6b (made of electrically conductive material) coated with a magnetostrictive material 26, the coatings 26 being fused together in the space separating the paired fiber strands. Suitable magnetostrictive material includes nickel and the rare-earth iron material known as Terfenol-D ($Tb_xDy_{1-x}Fe_2$). In this embodiment, the electrically conductive fiber strands 6a and 6b are shorted together at their distal ends using electrically conductive material 30. In response to pulsation, the electromagnetic field produced by the shorted fiber strands 6a and 6b due to the electric current pulse from the pulser is converted to mechanical vibration of the magnetostrictive material 26 and then into acoustic waves. Alternatively, a single electrically conductive fiber strand coated with magnetostrictive material can be folded and then fused together to achieve the same effect.

Figure 5:
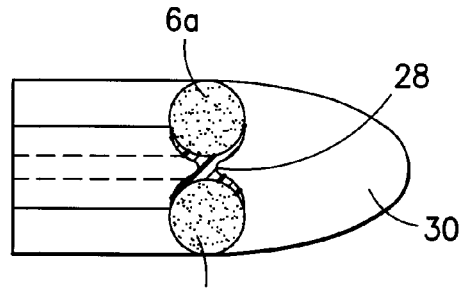
FIG. 5 is a diagram showing a side view with cross section of a pair of partially coated electrically conductive fiber strands fused together along their length by a partial coating made of magnetostrictive material. Again the electrically conductive fiber strands are shorted at their ends.

Yet another exemplary construction is shown in FIG. 5. In accordance with this embodiment, each acoustic source comprises a pair of uncoated fiber strands 6a, 6b (made of electrically conductive material) which are held together, separated and electrically insulated from each other by magnetostrictive material 28. Again, a major portion of the surface area of each fiber strand 6a, 6b is bare to the surrounding epoxy medium to maximize structural strength. In response to a current pulse from the pulser, an electromagnetic field is produced between the fiber strands 6a and 6b, which in turn induces the magnetostrictive material 28 to generate an acoustic wave that propagates through the surrounding matrix of the composite part.

In accordance with a further alternative embodiment, a pair of small-gauge electrically conductive fiber strands coated with magnetostrictive material can be twisted together to form an acoustic source.

In accordance with other alternative embodiments, the magnetostrictive coatings 26 and 28 respectively seen in FIGS. 4 and 5 can be replaced with coatings made of insulating material that does not have magnetostrictive properties. Instead the magnetostrictive material can be incorporated in the fiber strands 6a, 6b. For example, since carbon nanotubes and other nanowires have magnetostrictive properties, each fiber strand 6a, 6b may be supplemented with nanotubes or nanowires to enhance overall structural performance. For example, carbon nanotubes and other nanowires may be used to convert small pulses of electric current to sound. Other mechanical actuator modes are known. In particular, the fiber strands 6a and 6b could be made of carbon filaments supplemented by carbon nanotubes or they could be made exclusively of carbon nanotubes. By using carbon nanotubes, the acoustic sources would comprise a fiber material stronger than the current state-of-the-art carbon (graphite) fiber strands, and would mitigate the aerospace manufacturing concern that overall quality of the final part was being mitigated for short-term qualification convenience. Alternatively, nanotubes made of a material different than carbon can be used.

In accordance with a further aspect, the external transducers may be supported by an external flexible substrate such as a blanket which is wrapped around the composite part. The external substrate, when stretched out, acts to maintain predefined distances between the external transducers. Optionally, the external fixture incorporates a multiplicity of locating markers which can be used in conjunction with painted lines or an inscribed figure on the composite part being inspected to ensure repeatable positioning of the external fixture.

Figure 6:
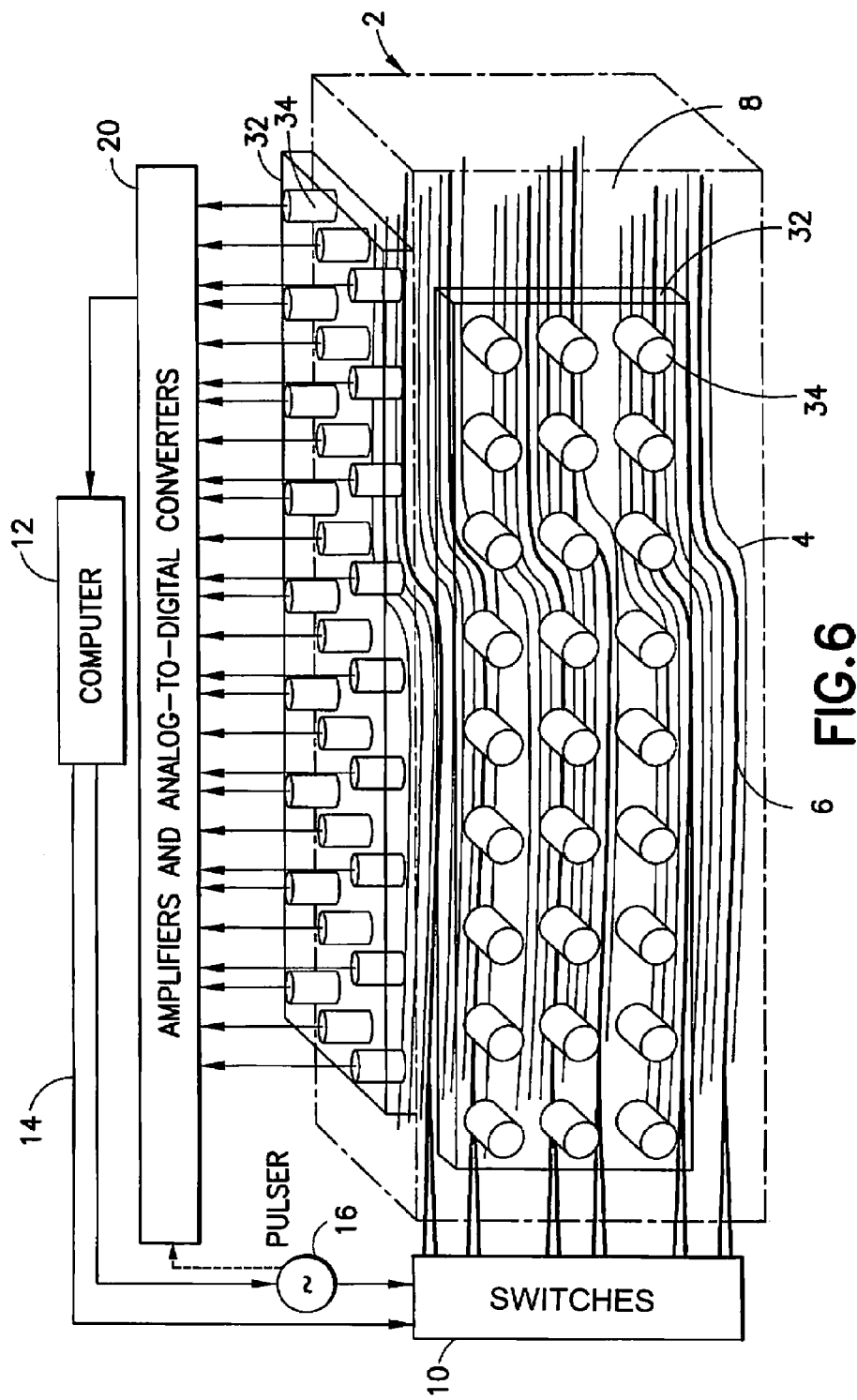
FIG. 6 is a diagram showing a system for non-destructive evaluation of a composite part in accordance with another embodiment.

In accordance with a further embodiment shown in FIG. 6, each face of the composite part 2 may have a respective fixed array of external transducers attached thereto. In this example, each fixed array comprises a multiplicity of precisely spaced piezoelectric ceramic rods 34 embedded in a polymeric matrix 32. Suitable fixed arrays of piezoelectric transducers are commercially available from Materials Systems, Inc. and Blatek, Inc. (State College, Pa., U.S.A.). Each piezoelectric ceramic rod 34 outputs an electrical signal to a corresponding amplifier in response to an impinging acoustic wave.

The methodology disclosed hereinabove will allow thick complex composite parts to be manufactured with lower allowables, giving assurance that they are manufactured correctly and with sufficient strength, while weighing and costing less. In cases where the composite part is a laminate comprising a multiplicity of plies, each ply may be fabricated with acoustic sources embedded therein and interleaved and co-aligned with the mutually parallel structural fiber strands of that ply. Thus each ply of the cured composite part can be separately inspected to determine whether the structural fiber strands in that ply have the correct location and orientation (i.e., fiber angle).

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention. For example, transducing fiber strands could be embedded in a polymeric matrix that is devoid of other reinforcement (such as structural fiber strands commonly present in fiber-reinforced plastic), for the purpose of detecting defects in that polymeric matrix.

The computer disclosed may have multiple processors. For example, one processor for driving the internal transducers, another processor for processing signals derived from the signals outputted by the external transducers, a third for executing tomographic algorithms, and a fourth processor for controlling a monitor to display tomographic images. Alternatively, these functions may be performed by separate computers that communicate. As used in the claims, the term "computer system" should be construed broadly to encompass a single computer or processor as well as multiple computers or processors.

The method claims set forth hereinafter should not be construed to require that all steps of the method be performed in alphabetical order or in the order in which they are recited.

The invention claimed is:

1. A fiber-reinforced composite part comprising a multiplicity of plies, wherein at least one of said multiplicity of plies comprises:
   a matrix of polymeric material;
   a multiplicity of structural fiber strands embedded in said polymeric matrix; and
   a multiplicity of linear electromagnetic-to-acoustic transducers embedded in said polymeric matrix and interspersed with said structural fiber strands,
   wherein each of said electromagnetic-to-acoustic transducers comprises a pair of fiber strands, said fiber strands of said electromagnetic-to-acoustic transducers and said structural fiber strands being mutually parallel.

2. The fiber-reinforced composite part as recited in claim 1, wherein said fiber strands of said electromagnetic-to-acoustic transducers are made of electrically conductive material, said electromagnetic-to-acoustic transducers further comprise piezoelectric or magnetostrictive material, and said fiber strands of said electromagnetic-to-acoustic transducers are coated or otherwise separated by said piezoelectric or magnetostrictive material.

3. The fiber-reinforced composite part as recited in claim 2, wherein the fiber strands of each of said pairs of fiber strands are shorted together.

4. The fiber-reinforced composite part as recited in claim 1, wherein said fiber strands of said electromagnetic-to-acoustic transducers and said structural fiber strands comprise carbon.

5. The fiber-reinforced composite part as recited in claim 1, wherein each of said fiber strands of said electromagnetic-to-acoustic transducers further comprises a multiplicity of nanotubes.

6. A method for non-destructive inspection of a composite part, comprising:
(a) activating a multiplicity of linear acoustic sources embedded in a polymeric matrix of the composite part in sequence, thereby causing acoustic waves to emanate from each acoustic source and propagate toward external surfaces of the composite part; and
(b) transducing acoustic waves received at external surfaces of the composite part from each acoustic source into electric signals having characteristics indicative of the run of each acoustic source,
wherein each linear acoustic source comprises a pair of fiber strands made of electrically conductive material and coated or otherwise separated by piezoelectric or magnetostrictive material.

7. The method as recited in claim 6, wherein the composite part comprises a multiplicity of plies, each ply comprising structural fiber strands, and at least one of the plies comprising linear acoustic sources which are interspersed and co-aligned with the structural fiber strands in that one ply.

8. The method as recited in claim 6, further comprising acoustically coupling a multiplicity of acoustic-to-electric transducers to external surfaces of the composite part, wherein step (b) is performed by the acoustic-to-electric transducers.

9. The method as recited in claim 6, further comprising processing the electric signals to determine positions of the runs of the acoustic sources.

10. The method as recited in claim 9, wherein said processing comprises interpolating the amplitudes or times of arrival of an acoustic wave detected by a pair of acoustic-to-electric transducers that detect the greatest amplitudes for that acoustic wave.

11. The method as recited in claim 9, wherein said processing comprises dividing the electric signals into a direct path response and an indirect path response.

12. The method as recited in claim 9, wherein said processing comprises amplifying the electric signals using phase-locked amplification.

13. A system comprising:
a composite part comprising a multiplicity of plies, wherein at least one of said multiplicity of plies comprises a polymeric matrix and a multiplicity of linear electromagnetic-to-acoustic transducers embedded in said polymeric matrix;
a pulser for outputting pulsed electrical energy;
a multiplicity of switches connected to said pulser and respectively connected to said linear electromagnetic-to-acoustic transducers, each of said switches electrically coupling a respective linear electromagnetic-to-acoustic transducer to said pulser when said switch is closed and said pulser is outputting pulsed electrical energy; and
a computer system programmed to control said switches to select which linear electromagnetic-to-acoustic transducer receives pulsed electrical energy from said pulser.

14. The system as recited in claim 13, further comprising a multiplicity of acoustic-to-electric transducers arranged outside said composite part and acoustically coupled to external surfaces of said composite part, wherein said computer system is further programmed to process electric signals produced by said acoustic-to-electric transducers to determine a position of a run of the pulsed linear electromagnetic-to-acoustic transducer.

15. The system as recited in claim 14, further comprising a multiplicity of phase-locked amplifiers connected to said computer system and respectively connected to said multiplicity of acoustic-to-electric transducers.

16. The system as recited in claim 14, wherein said computer system is programmed to interpolate the amplitudes or times of arrival of an acoustic wave detected by a pair of acoustic-to-electric transducers that detect the greatest amplitudes for that acoustic wave.

17. The system as recited in claim 14, wherein said computer system is programmed to divide the electric signals into a direct path response and an indirect path response.

18. The system as recited in claim 13, wherein said at least one ply of said composite part further comprises a multiplicity of structural fiber strands, said linear electromagnetic-to-acoustic transducers of each ply being interspersed with the structural fiber strands in that ply.

19. The system as recited in claim 18, wherein each electromagnetic-to-acoustic transducer comprises a pair of fiber strands, said fiber strands of said electromagnetic-to-acoustic transducers and said structural fiber strands being mutually parallel in said at least one ply.

20. The system as recited in claim 19, wherein each fiber strand further comprises a multiplicity of nanotubes.

21. The system as recited in claim 13, wherein each linear electromagnetic-to-acoustic transducer comprises a pair of fiber strands made of electrically conductive material and coated or otherwise separated by piezoelectric or magnetostrictive material.

22. The system as recited in claim 13, wherein each linear electromagnetic-to-acoustic transducer comprises a first electrical conductor, a second electrical conductor surrounding said first electrical conductor, and piezoelectric material occupying space between said first and second electrical conductors.

23. The system as recited in claim 13, further comprising a flexible substrate that is wrapped around said composite part, wherein said multiplicity of acoustic-to-electric transducers are secured to said substrate.

* * * * *